(12) United States Patent (10) Patent No.: US 8,372,043 B2
Grimm et al. (45) Date of Patent: Feb. 12, 2013

(54) DEVICES AND METHODS FOR FLUID ADMINISTRATION

(75) Inventors: Kevin Grimm, Danville, PA (US); Lauren Marie Shafer, Whitehall, PA (US); Travis Snyer, Pittsburgh, PA (US); Rachel Elise Zielinski, Manchester, PA (US); Daniel George Johnson, New Columbia, PA (US)

(73) Assignee: Geisinger Clinic, Danville, PA (US)

( * ) Notice: Subject to any disclaimer, the term of this patent is extended or adjusted under 35 U.S.C. 154(b) by 446 days.

(21) Appl. No.: 12/598,103

(22) PCT Filed: May 1, 2008

(86) PCT No.: PCT/US2008/062272
§ 371 (c)(1),
(2), (4) Date: Aug. 31, 2010

(87) PCT Pub. No.: WO2008/137578
PCT Pub. Date: Nov. 13, 2008

(65) Prior Publication Data
US 2011/0046602 A1 Feb. 24, 2011

Related U.S. Application Data

(60) Provisional application No. 60/915,304, filed on May 1, 2007.

(51) Int. Cl.
*A61M 5/00* (2006.01)

(52) U.S. Cl. ........................ 604/191; 604/181; 604/93.01
(58) Field of Classification Search .................. 604/191, 604/93.01, 181, 151, 152
See application file for complete search history.

(56) References Cited

U.S. PATENT DOCUMENTS

| | | | |
|---|---|---|---|
| 4,534,764 A | 8/1985 | Mittleman et al. | |
| 5,431,185 A | 7/1995 | Shannon et al. | |
| 5,697,904 A | 12/1997 | Raines et al. | |
| 5,720,731 A | 2/1998 | Aramata et al. | |
| 5,743,886 A * | 4/1998 | Lynn et al. | 604/191 |
| 5,772,630 A | 6/1998 | Ljungquist | |
| 5,899,881 A | 5/1999 | Grimard et al. | |
| 5,971,953 A * | 10/1999 | Bachynsky | 604/90 |
| 6,364,861 B1 | 4/2002 | Feith et al. | |
| 6,508,791 B1 | 1/2003 | Guerrero | |
| 6,866,653 B2 | 3/2005 | Bae | |
| 2002/0156431 A1 | 10/2002 | Feith et al. | |
| 2004/0243069 A1 | 12/2004 | Feith et al. | |

FOREIGN PATENT DOCUMENTS

WO WO 2008/137578 11/2008

* cited by examiner

*Primary Examiner* — Nicholas Lucchesi
*Assistant Examiner* — Leah Stohr
(74) *Attorney, Agent, or Firm* — Woodcock Washburn LLP

(57) ABSTRACT

Improved fluid delivery devices and systems are disclosed, including drug delivery devices and systems, and methods that permit, inter alia, the rapid sequential delivery of two or more fluids to a single external fluid flow or intravenous line.

29 Claims, 8 Drawing Sheets

DEVICES AND METHODS FOR FLUID ADMINISTRATION

CROSS-REFERENCE TO RELATED APPLICATIONS

This application is the National Stage of International Application No. PCT/US2008/062272, filed May 1, 2008, which claims the benefit of U.S. Provisional Application No. 60/915,304, filed May 1, 2007, the disclosures of which are incorporated herein by reference in their entirety.

FIELD OF THE INVENTION

The present invention pertains to devices and methods for administration of fluid agents, and more particularly to devices and methods of administration of pharmaceutical agents. Also provided are methods for improved delivery of fluid agents.

BACKGROUND OF THE INVENTION

Infusion of fluid components in rapid succession is required by a variety of medical and non-medical processes.

One example is the administration of the tachycardia drug adenosine. Adenosine is both an endogenous nucleoside and a drug that is commonly used as an antiarrhythmic agent and sometimes in cardiac diagnostic testing. Adenosine is typically employed in the form of a sterile, nonpyrogenic solution for intravenous injection. The drug adenosine possesses a half-life of less than 10 seconds and a duration of one to two minutes. Therefore, to achieve administration of active drug, adenosine often is delivered by rapid intravenous bolus over 1-2 seconds followed immediately by a rapid saline flush to aid in the injection reaching the subject's systemic circulation.

Traditional adenosine administration involves injecting the drug using a syringe, removing the empty adenosine syringe from the intravenous apparatus y-port, attaching a second, saline-filled syringe to the y-port, and then delivering the saline flush through the same port as the adenosine injection. Another conventional manner of adenosine administration includes employing a three-way stopcock and manipulating the stopcock valve in the intervening time between delivery of the medication and flush administration. The administration of adenosine often occurs in the emergency room context, where rapid and accurate completion of clinical protocols can be essential to the recovery of the patient.

Given the criticality of the speed of administration of adenosine to its effectiveness, there exists a need for methods and devices that alleviate the difficulty associated with the conventional process of adenosine administration. More generally, there exists a need for improved methods and devices for the administration other fluid agents that require rapid sequential delivery.

Other inventors have developed approaches to the problem by providing syringes and cartridges with a plurality of stoppers to allow sequential delivery of a therapeutic agent and a flush agent. See, e.g., U.S. Pat. Nos. 6,866,653, 5,899,881, 5,772,630, and 5,720,731. These devices and methods do not permit loading of the therapeutic agent and the flush agent through the same outlet through which the agents are delivered.

SUMMARY OF THE INVENTION

Provided are dual-stopper syringe devices and sequential liquid agent delivery methods including a chamber including an outlet, a bypass channel having a front end and rear end, and a stopper assembly, including a front stopper, a rear stopper, a piston attached to the rear stopper and adapted to receive a pushing or pulling action from a user to actuate the syringe, and a rod including a backstop, the rod being affixed to the front stopper and slidably connected to the rear stopper, the rod slidably penetrating through the rear stopper such that the rear stopper is adapted to slide along the rod between the front stopper and the backstop, the backstop limiting the rearward movement of the rear stopper relative to the front stopper.

The dual-stopper syringe devices and sequential liquid agent delivery methods include syringes capable of having an unloaded position, a flush agent loading position, and a therapeutic agent loading position, in the unloaded position, the front stopper and the rear stopper are located proximate the chamber outlet, in the flush agent loading position, the front stopper is located proximate the chamber outlet, the rear stopper is spaced apart from the front stopper to define a flush chamber, and the rear end of the bypass channel is open to the flush chamber, in the therapeutic agent loading position, the front stopper is spaced apart from the outlet to define a therapeutic agent chamber, the rear stopper is spaced apart from the front stopper and located proximate the backstop, and the rear end of the bypass channel is either blocked by the front stopper or open to the therapeutic agent chamber, whereby in the unloaded position and the flush agent loading position, the piston moves the rear stopper away from the outlet and away from the front stopper when pulled, and whereby in the therapeutic agent loading position, the piston moves the front stopper and rear stopper away from the outlet when pulled.

Provided are plunger-less fluid administration cartridges comprising: a chamber having a body, an inlet port, and an outlet port at opposing ends; a bypass line connecting the chamber body to the outlet port and enabling flow therebetween; a barrier stopper located in the chamber body and movable between a ready position and an actuated position; the stopper, in the ready position, (i) is spaced apart from the outlet port to form a drug compartment of the chamber and (ii) blocks flow of a working fluid into the bypass line; the stopper, in the actuated position, is located proximate the outlet port and enables flow of the working fluid through the bypass line from the inlet port to the outlet port; whereby moving the stopper from the ready position to the actuated position ejects fluid from the drug compartment through the outlet port.

Also disclosed are fluid delivery devices comprising a cartridge having a central chamber having two opposing ends; at the first end of said central chamber, a fluid inlet; at the second end of said central chamber, an outlet channel, and a fluid outlet disposed between said central chamber and said outlet channel and permitting fluid flow between said central chamber and said fluid outlet; a bypass conduit permitting fluid flow directly between said central chamber and said outlet channel and not via said fluid outlet; a stopper disposed within said central chamber, said stopper being capable of responding to fluid pressure resulting from fluid being pushed through said fluid inlet and into said central chamber, wherein said responding includes a first stage comprising moving within said central chamber in the direction away from said first end of said central chamber, and wherein said responding also includes a second stage comprising moving within said central chamber whereby said stopper is positioned such that fluid flow from said central chamber into said bypass conduit is enabled.

There are also provided methods of delivering a therapeutic agent comprising the steps of pressurizing said therapeutic agent within a drug chamber by introducing a working fluid into a working chamber that is separated from said drug chamber by a movable stopper, said stopper responding to the introducing of said working fluid into said working chamber by pressurizing said therapeutic agent; wherein said pressurizing forces said therapeutic agent into a delivery channel via an outlet port that is in fluid communication with said drug chamber; and, wherein the introducing of the working fluid into the working chamber moves said stopper to a position whereby the working fluid can flow between said working chamber and said delivery channel via a bypass conduit.

Also disclosed are methods of delivering a fluid agent comprising the steps of providing a cartridge including a working fluid chamber proximate a cartridge inlet, a fluid agent chamber proximate a cartridge outlet, a moveable stopper therebetween, and a bypass conduit; introducing a working fluid into the working chamber such that the stopper moves from a ready position, in which the stopper blocks flow from entering the bypass conduit, in the direction of the cartridge outlet to an actuated position, whereby said stopper movement (i) pushes at least a portion of the fluid agent from the cartridge and (ii) unblocks the bypass conduit to enable working fluid flow from the working fluid chamber.

DETAILED DESCRIPTION OF ILLUSTRATIVE EMBODIMENTS

Provided are improved fluid delivery devices, including drug delivery devices, and methods that permit, inter alia, the rapid sequential delivery of two or more fluids to a single external fluid flow or intravenous line. One, some, or all of the two or more fluids may comprise a therapeutic agent.

For example, the administration of liquid adenosine to a patient is particularly prone to complications, since compound half-life is extremely brief and injection must be followed immediately by a rapid saline flush to ensure systemic distribution of drug. Additionally, the administration of adenosine often occurs in the emergency room context, where rapid and accurate completion of clinical protocols can aid the recovery of the patient. Other drugs with volatile kinetic profiles and drugs that must be "chased" with or preceded by one or more other fluids (such as saline) are similarly difficult to dispense and are therefore subject to complications during clinical administration. The instant devices and methods address the need for ways to ensure the quick, simple, and effective administration of certain drugs, including, inter alia, adenosine, atropine, epinephrine, lidocaine, sodium bicarbonate, and amiodarone. The inventive devices and methods also permit delivery of two or more drugs in rapid succession.

Figure 1:
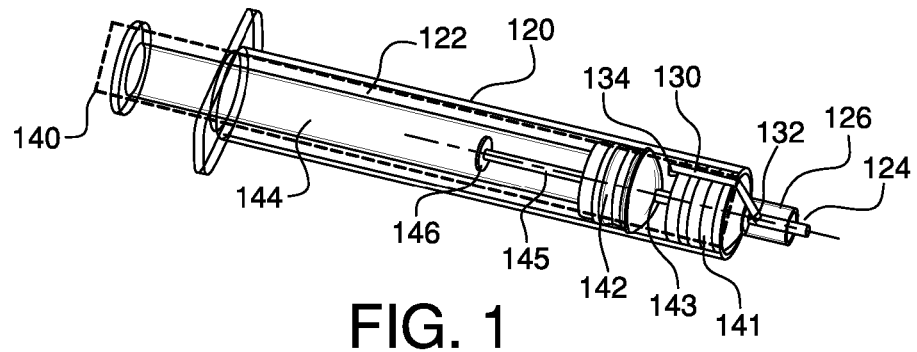
FIG. 1 is a perspective view of a dual-stopper syringe, with the stoppers in the unloaded position.
Figure 2A:
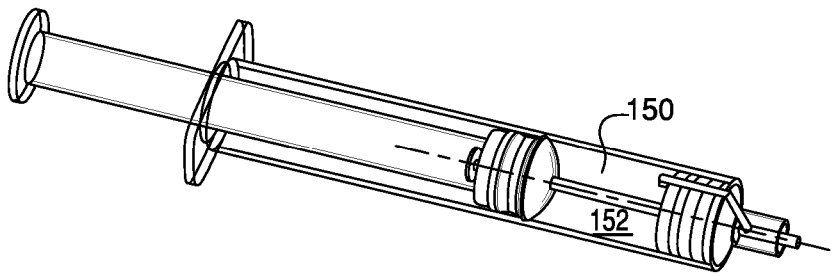
FIG. 2A is a perspective view of a dual-stopper syringe, with the stoppers in the flush agent loading or flush agent delivery position.
Figure 2B:
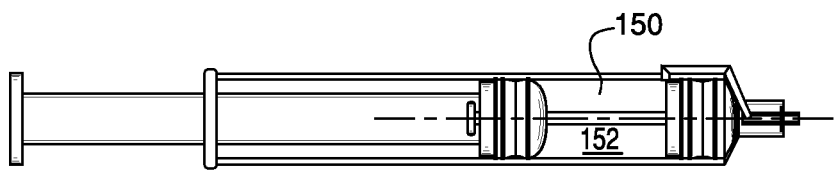
FIG. 2B is a side view of the dual-stopper syringe depicted in FIG. 2A.
Figure 3:
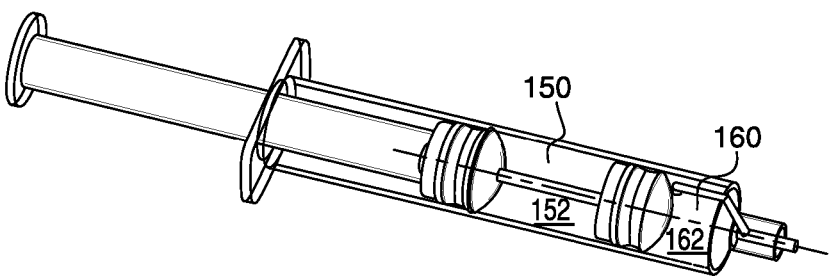
FIG. 3 is a perspective view of a dual-stopper syringe, with the stoppers in the therapeutic agent loading or therapeutic agent delivery position.

Referring to FIGS. 1-3 to illustrate a preferred structure and method of the present invention, a fluid delivery device and method includes a dual-stopper syringe 110 that has a barrel 120, a bypass channel 130, and a stopper assembly 140. Syringe 110, depending on its mode of use, may define a flush agent chamber 150 and a therapeutic agent chamber 160. Barrel 120 includes an internal space defining a chamber 122 and includes an outlet 124. Bypass channel 130 defines a front end 132 and a rear end 134. Stopper assembly 140 includes a front stopper 141, a rear stopper 142 including a rod aperture 143, a piston 144, and a rod 145 including a backstop 146. Flush agent chamber 150 may contain a flush agent 152, such as saline. Therapeutic agent chamber 160 may contain a therapeutic agent 162.

Barrel 120 preferably is cylindrical, having an outer cross-sectional profile that is approximately circular, but it may also have other outer cross-sectional profiles, including oval, square, rectangular, and octagonal. Chamber 122 is preferably cylindrical, having a cross-sectional profile that is approximately circular, but it may also have other cross-sectional profiles, including oval, square, rectangular, and octagonal. Chamber 122 may also have a cross-sectional profile that varies in size as it approaches outlet 124, resulting in a tapered profile. The internal walls of chamber 122 preferably are smooth.

Chamber 122 preferably has a volume of 10 ml, but it may have any volume, including standard syringe volumes such as 3 ml, 5 ml, 20 ml, and 50 ml, and it may also have any non-standard volume, depending on the particular desired therapeutic agent 162 and the particular patient size, gender, weight, and physical condition. Barrel 120 preferably is made of a conventional plastic, such as polypropylene or polyethylene, that is inert with respect to a particular desired therapeutic agent 162. Barrel 120 may also be made of other plastics or other materials, such as metal, glass, ceramic, or any other material that can effectively contain the desired therapeutic agent 162. Outlet 124 is the port through which the desired flush agent 152 and therapeutic agent 162 is drawn into chamber 122 and discharged out of chamber 122. Outlet 124 preferably is shaped in a luer-lock or luer-slip configuration, but it may have other shapes or dimensions, depending on the size and shape of needle (not shown) or fluid flow line (not shown) that will be coupled to outlet 124.

Outlet 124 optionally forms an outlet channel 126 that is in fluid communication with chamber 122. The internal diameter of outlet channel 126 is preferably smaller than that of chamber 122. The external profile of outlet 124 is preferably smooth and capable of sealably engaging a fluid flow line such that fluid flowing through outlet 124 will enter the fluid flow line, and no leakage will occur at the junction between outlet 124 and the fluid flow line.

Dual-stopper syringe 110 may be used in conjunction with any dedicated line, including but not limited to an IV line, a catheter, or a central line. As used herein, the phrase "dedicated line" generally refers to any line for the delivery of fluid. Therefore, in preferred embodiments, dual-stopper syringe 110 may be used as a component in any fluid delivery system that includes a dedicated line. In preferred embodiments, outlet 124 is adapted for connection to a dedicated line.

In a preferred embodiment, the outlet channel 126 comprises a male luer connector. Both the internal bore and the external surface profile of outlet channel 126 are preferably smooth and capable of engaging a fluid flow line in a "luer slip" configuration; alternatively, the external surface of outlet channel 126 can feature threading in order to accommodate a fluid flow line in a "luer lock" arrangement or any other structure for attaching a tubing or another device, as will be understood by persons familiar with conventional fluid administration devices.

For delivery of multiple doses of drug or multiple different drug substances (not shown), a plurality of dual-stopper syringes 110 may be arranged in parallel, each in fluid communication with an outlet line and fluid delivery unit via their respective outlets 124. For example, if a series of three syringes are used, a first therapeutic agent 162, a second therapeutic agent 162, and a third therapeutic agent 162, respectively, may be loaded into the therapeutic agent chambers 160 of the syringes, and this arrangement can be used to deliver the therapeutic agents 162 of the respective syringes simultaneously, two at a time, or in fully staggered fashion. The inventive devices impose no limitations on the potential choices for such arrangements.

Bypass channel 130 is a channel through which fluid can flow, and includes front end 132 and a rear end 134. Bypass channel 130 preferably provides a fluid flow channel between chamber 122 and outlet channel 126. During "flush agent loading," flush agent 152 in outlet channel 126 enters bypass channel 130 through front end 132 and exits through rear end 134 into chamber 122. During "flush agent delivery," flush agent 152 in chamber 122 enters bypass channel 130 through rear end 134 and exits through front end 134 into outlet channel 126. Bypass channel 130 may be constructed from hollow tubular material, formed from a bore through a solid substance, e.g., through drilling, or formed in accordance with other methods, a number of which are readily appreciated by those familiar with conventional fluid administration device fabrication.

In the preferred embodiment shown in FIGS. 1-3, bypass channel 130 is of a tubular construction, such that only front end 132 and rear end 134 of bypass channel 130 are open to chamber 122 and outlet channel 126. However, in other embodiments (not shown), bypass channel 130 has a slot or slotted configuration, in which the entire length of bypass channel 130, from front end 132 to rear end 134, or a portion thereof, is open to chamber 122 and outlet channel 126. Any style of bypass channel 130 is contemplated in the inventive device, so long as bypass channel 130 is in fluid communication with flush agent chamber 150 during the flush agent loading or flush agent delivery positions of stopper assembly 140 (see FIGS. 2A and 2B and discussion below), and bypass channel 130 is not in fluid communication with flush agent chamber 150 during the therapeutic agent loading or therapeutic agent delivery positions of stopper assembly 140 (see FIG. 3 and discussion below).

Front stopper 141 and rear stopper 142 are disposed within chamber 122 and are movable relative to each other and among different positions within chamber 122. Front stopper 141 is in sealing contact with the interior surface of barrel 120 such that it prevents fluid communication between flush agent chamber 150 or outlet channel 126 and therapeutic agent chamber 160 except via bypass channel 130. Accordingly, front stopper 141 prevents fluid that flows into chamber 122 via outlet channel 126 from reaching flush agent chamber 150 if rear end 134 of bypass channel 130 is not open to flush agent chamber 150. Rear stopper 142 is in sealing contact with the interior surface of barrel 120 such that it prevents fluid communication between flush agent chamber 150 and the portion of chamber 122 farthest away from outlet 124 where piston 144 is located. Piston 144 is attached to rear stopper 142 and adapted to receive a pushing or pulling action from a user to actuate dual-stopper syringe 110, i.e., to discharge a fluid out of chamber 122 or draw a fluid into chamber 122.

Front stopper 141 and rear stopper 142 comprise movable barriers that may be solid or hollow and preferably are constructed from at least one fluid-impermeable material. Exemplary fluid-impermeable materials include rubber, plastic, and combinations thereof, but other materials may be used, depending on the particular flush agent 152 and therapeutic agent 162 used. Front stopper 141 and rear stopper 142 preferably are cylindrical or disk-like in shape with substantially circular cross-sectional profiles, although the stoppers 141 and 142 may alternatively adopt other three-dimensional configurations, such as that of a polyhedron, e.g., a rectangular polyhedron having square or rectangular leading and trailing ends, to match corresponding cross-sectional shapes of chamber 122.

The outer surfaces of front stopper 141 and rear stopper 142 that contact the inner walls of chamber 122 may comprise one or more annular ribs disposed perpendicularly with respect to the longitudinal axis X of stoppers 141 and 142. The ribs can circumscribe the central portion of stoppers 141 and 142 at various locations along the length thereof such that only the ribs are in slidable contact with the inner walls of chamber 122. For example, stoppers 141 and 142 may include one or more spaces or recesses that circumscribe the outer surface of stoppers 141 and 142, with a rubber o-ring or gasket disposed within each space or recess, such that the outer edge of each o-ring or gasket contacts the inner walls of chamber 122 and thereby forms a seal about the entire circumference of the inner walls of chamber 122.

In another embodiment (not shown), each front stopper 141 and rear stopper 142 comprises two or more discs each disposed perpendicularly to the longitudinal axis X of barrel 120, and joined by one or more support members (not shown) that preserve the orientation of the discs and that cause the discs to move synchronously, i.e., prevent the discs from moving relative to one another. In this embodiment, each stopper 141 and 142 may resemble a barbell, with the "weights" being represented by the discs, and a support member fulfilling the role of the "bar" (although more than one support member may be employed in the current embodiment), the "weights" being fixably attached to the "bar". The outer edges of the discs preferably comprise material that creates a slidable seal between the outer edges of front stopper 141 and rear stopper 142 and the inner walls of chamber 122; for example, the outer edges may comprise rubber. In this embodiment, when stoppers 141 and 142 deployed within chamber 122, the space(s) between the discs within each stopper 141 or 142 are not exposed to the channel space(s) on the other side of the discs, and fluid cannot flow therebetween. Other surface profiles and configurations for stoppers 141 and 142 may be used, with the proviso that stoppers 141 and 142 must be able to move relative to each other and relative to the inner walls of chamber 122, and stoppers 141 and 142 should be able to prevent the flow of fluid through or around stoppers 141 and 142.

Stopper assembly 140 includes a rod 145 comprising a backstop 146 Rear stopper 142 is able to slide back and forth along rod 145 between front stopper 141 and backstop 146. Rear stopper 142 can slide along rod 145 via the use of rod aperture 143, which is an aperture that penetrates completely through rear stopper 142 in the longitudinal direction X of barrel 120. The diameter of rod aperture 143 is sized large enough relative to the diameter of rod 145 to allow rear stopper 142 to slide back and forth along rod 145 when piston 144 is pushed or pulled by a user, while at the same time, the diameter of rod aperture 143 is sized small enough relative to the diameter of rod 145 to prevent liquid in flush agent chamber 150 from leaking into the portion of chamber 122 farthest away from outlet 124 where piston 144 is located. The relative diameters of rod aperture 143 and rod 145 may be fine-tuned such that a desired friction force is achieved upon pushing or pulling of piston 144.

One end of rod 145 is attached to front stopper 141, while the other end of rod 145 penetrates completely through rear stopper 142 and terminates at the included backstop 146. This configuration of rod 145 and backstop 146 allows rear stopper 142 to slide towards front stopper 141 until rear stopper 142 touches front stopper 141, and it allows rear stopper 142 to slide away front stopper 141 until its further motion is prevented by backstop 146.

The length of rod 145 will be determined based on the desired volume of flush agent 152 necessary to effectively administer a particular therapeutic agent 162. The combination of the diameter of chamber 122 and the length of rod 145 determines the volume of flush agent 152 that can be contained in flush agent chamber 150. The length of rod 145 may be any length that allows the desired volume of flush agent 152 to be contained in flush agent chamber 150.

The diameter of backstop 146 in a direction perpendicular to the longitudinal direction X of barrel 120 is large enough relative to rod aperture 143 to effectively limit the movement of rear stopper 142 in the longitudinal direction X of barrel 120 when rear stopper 142 has moved away front stopper 141 such that the maximum desired amount of flush agent 152 is contained in flush agent chamber 150.

In the embodiment shown in FIGS. 1-3, rod 145 and backstop 146 have a small enough diameter relative to the inner diameter of piston 144 (which contains some interior hollow area) such that rod 145 and backstop 146 fit inside piston 144 and remain inside piston 144 as rear stopper 142 travels back and forth along rod 145. In some embodiments, the diameter of backstop 146 may be fine-tuned relative to the inner diameter of piston 144, such that the motion of backstop 146 against the interior walls of piston 144 produces an additional friction force and/or the contact between backstop 146 and the interior of walls piston 144 allows for an additional constraint of the motion of rear stopper 142 along the longitudinal X axis of barrel 120, preventing rear stopper 142 from tilting relative to the longitudinal X axis of barrel 120, as rear stopper 142 moves relative to front stopper 141.

In other embodiments (not shown), there may optionally be a plurality of rods 145 and backstops 146, and they may be optionally positioned at various distances from the longitudinal X axis of barrel 120. In some embodiments, a plurality of rods 145 may penetrate through a plurality of rod apertures 143, arranged around the outer perimeter of rear stopper 142, such that when the rear stopper 142 moves towards front stopper 141, the rods 145 extend through rear stopper 142 to the outside of piston 144, rather than through the inside of piston 144 as in the embodiment shown in FIGS. 1-3.

One, some, or all of the two or more fluids contained in flush agent chamber 150 and therapeutic agent chamber 160 may comprise a therapeutic agent 162. The flush agent 152 may comprise, for example, a diluent or carrier (such as saline), or it may comprise a beneficial therapeutic agent 162, such that the administration of the therapeutic agent 162 as delivered from therapeutic agent chamber 160 may be followed by the administration of a second therapeutic agent 162 as delivered from the flush agent chamber 150.

The construction of the instant dual-stopper syringes may be accomplished in accordance with techniques that are widely understood among those skilled in the art. The syringe and its various components as described herein may be molded from suitable materials, such as various plastic materials, using such molding techniques as thermoplastic and thermoset injection molding, blow molding, rotational molding, thermoforming, structural foam molding, compression molding, resin transfer molding (RTM), or others. Alternatively, the syringe and its components may be machined, for example, by drilling passages for such features as bypass channel 130, chamber 122, and outlet channel 126. A combination of molding and machining techniques may also be used. Chamber 122 and bypass channel 130 may be formed from a continuous block. For example, a manufacturer may form chamber 122 and bypass channel 130 by hollowing out portions of a single block of material, or the manufacturer may form chamber 122 and bypass channel 130 by hollowing out half of these structures from a first block, the other half of these structures from a second block, and then joining the first and second blocks to form complete chamber 122 and bypass channel 130 structures. All methods of constructing the chamber 122 and bypass channel 130 structures, and the other structures of the instant devices, are contemplated as being within the scope of the present invention.

Preferable materials for manufacturing the components of dual-stopper syringe 110 include those that are compatible with medical treatment of human subjects, and to this end, polypropylene is a preferred material for many of the components of the present device. With regard to stoppers 141 and 142, those components preferably include one or more integral sections, such as ribs or discs, that provide a slidable seal with the interior walls of chamber 122; these integral sections may comprise any suitable material or combination of materials, including natural or synthetic "rubber", such as, for example, Kalrez®, Simriz®, Viton®, Chemraz®, silicone, neoprene, and/or nitrile. The materials used for the construction of valves, fasteners, and connectors/luers, as well as the methods for the construction thereof, are readily appreciated by those skilled in the art, and all appropriate materials and means of construction are contemplated herein.

FIGS. 1-3 can be viewed in progression to illustrate the process by which a flush agent 152 is preferably drawn into flush agent chamber 150 and a therapeutic agent 162 is preferably drawn into therapeutic agent chamber 160.

FIG. 1 depicts stopper assembly 140 in the unloaded position. In this position, front stopper 141 and rear stopper 142 are located proximate outlet 124, and there is no fluid in chamber 122. This is the starting position of stopper assembly 140 from which a user can begin to draw fluids into chamber 122 through outlet 124. In this unloaded position, rear end 134 of bypass channel 130 is open to flush agent chamber 150, which is defined by the volume in chamber 122 that lies between front stopper 141 and rear stopper 142. As will be discussed below, FIG. 1 also depicts the final resting position of stopper assembly 140 after all fluids are dispensed through outlet 124.

FIGS. 2A and 2B depict stopper assembly 140 in the flush agent loading position. In this position, a user begins to draw flush agent 152 into flush agent chamber 150. This drawing action is accomplished by the user pulling piston 144 away from outlet 124. Piston 144 is attached to rear stopper 142, so when piston 144 is pulled away from outlet 124, rear stopper 142 is also pulled away from outlet 124. As rear stopper 142 is pulled back, rear stopper 142 slides away from front stopper 141 along rod 145. As rear stopper 142 slides away from outlet 124, front stopper 141 initially remains stationary, proximate outlet 124. As rear stopper 142 slides away from outlet 124, a pressure gradient is created between flush agent chamber 150 and outlet channel 126, which serves to draw flush agent 152 from outlet channel 126 to flush agent chamber 150, through bypass channel 130. Flush agent 152 enters outlet channel 126 from an external source. Flush agent 152 then enters bypass channel 130 via front end 132 and exits bypass channel 130 via rear end 134, where flush agent 152 enters flush agent chamber 150.

This flush agent loading action may continue until rear stopper 142 travels to the end of rod 145, and the motion of rear stopper 142 relative to front stopper 141 reaches the motion limit imposed by backstop 146. When rear stopper 142 reaches backstop 146, flush agent chamber 150 is fully-loaded with flush agent 152. When the user continues pulling back on piston 144, rear stopper 142 continues to move away from outlet 124, but the pulling force is transmitted through backstop 146 and rod 145 to front stopper 141, which also begins to move away from outlet 124. Very soon after front stopper 141 begins to move away from outlet 124, front stopper 141 blocks rear end 134 of bypass channel 130, which isolates flush agent chamber 150 from other portions of chamber 122. At this point, stopper assembly 140 is prepared for loading of therapeutic agent 162 into therapeutic agent chamber 160. As will be discussed below, FIGS. 2A and 2B also depict the flush agent delivery position of stopper assembly 140, which occurs while fluids are being expelled from chamber 122.

FIG. 3 depicts stopper assembly 140 in the therapeutic agent loading position. In this position, a user begins to draw therapeutic agent 162 into therapeutic agent chamber 160, preferably from a different fluid source than that which was used to draw flush agent 152. This drawing action is accomplished by the user pulling piston 144 further away from outlet 124. Because flush agent chamber 150 is fully-loaded with flush agent 152 and rear stopper 142 is proximate to backstop 146, when the user continues pulling back on piston 144, rear stopper 142 and front stopper 141 move in tandem away from outlet 124.

This movement of front stopper 141 away from outlet 124 creates a pressure gradient between therapeutic agent chamber 160 and outlet channel 126, which serves to draw therapeutic agent 162 from outlet channel 126 to therapeutic agent chamber 160. Therapeutic agent 162 enters outlet channel 126 from an external source. The user may continue the therapeutic agent loading process by continuing to pull back piston 144 further away from outlet 124, which will continue to result in more therapeutic agent 162 being drawn into therapeutic agent chamber 160. The user may continue the therapeutic agent loading process until the desired amount of therapeutic agent 162 is loaded into therapeutic agent chamber 160. The total volume of chamber 122 will limit the potential capacity of therapeutic agent chamber 160 to be filled with additional therapeutic agent 162, but the length or diameter of chamber 122 may be appropriately designed to accommodate the desired volume of therapeutic agent 162 in therapeutic agent chamber 160. It is not necessary that bypass channel 130 be used during therapeutic agent loading, because therapeutic agent chamber 160 and outlet channel 126 are fluidly connected.

FIG. 3 also depicts the therapeutic agent delivery position of stopper assembly 140, which occurs while fluids are being expelled from chamber 122. When a user has fluidly coupled outlet 124 to the desired target, e.g., the bloodstream of a patient, the user may commence delivery of the therapeutic agent. To achieve therapeutic agent delivery, the user follows the reverse steps of the process described above. The user begins to push or depress piston 144 towards outlet 124, which also pushes rear stopper 142 towards outlet 124 because piston 144 is attached to rear stopper 142. Furthermore, the force applied to push rear stopper 142 is transferred through flush agent 152, which is unable to leave flush agent chamber 150, to front stopper 141. The force from flush agent 152 pushes front stopper 141 in tandem with rear stopper 142, towards outlet 124. The force transferred to front stopper 141 creates a pressure gradient in therapeutic agent chamber 160 that causes therapeutic agent 162 to flow through outlet channel 126 out of dual-stopper syringe 110, and the into an optional feed line or other target.

As the user continues to push forward on piston 144, the therapeutic agent delivery process continues, expelling therapeutic agent 162 through outlet channel 126, until front stopper 141 is proximate outlet 124. At this time, all of therapeutic agent 162 preferably has been expelled from therapeutic agent chamber 160, but some therapeutic agent 162 may still remain in outlet channel 126. Also, when front stopper 141 reaches a position proximate to outlet 124, rear end 134 of bypass channel 130 becomes open to flush agent chamber 150. At this point, a user may begin the flush agent delivery process.

As mentioned above, FIGS. 2A and 2B also depict stopper assembly 140 in the flush agent delivery position. In this position, a user begins to discharge flush agent 152 from flush agent chamber 150 via bypass channel 130 and then via outlet channel 126. This delivery action is accomplished after completion of the therapeutic agent delivery process by the user continuing to push piston 144 towards outlet 124. As piston 144 pushes rear stopper 142 closer towards outlet 124, rear stopper 142 slides along rod 145 towards front stopper 141. Because rear end 134 of bypass channel 130 is open to flush agent chamber 150 a pressure gradient is created between flush agent chamber 150 and outlet channel 126. This pressure gradient forces flush agent 152 into bypass channel 130 via rear end 134 and out of bypass channel 130 via front end 132. Flush agent 152 is forced into outlet channel 126 and then out of dual-stopper syringe 110.

The delivery of flush agent 152 through outlet channel 126 flushes out substantially all of the remaining therapeutic agent 162 that remained in outlet channel 126 at the end of the therapeutic agent delivery process described above.

When the user finishes pushing piston 144 towards outlet 124 such that rear stopper 142 is proximate to front stopper 141, substantially all of flush agent 152 has been expelled from flush agent chamber 150 via bypass channel 130. After the therapeutic agent delivery process has been completed, stopper assembly 140 arrives at the final resting position, which is depicted by FIG. 1 as mentioned above.

Preferably, when stopper assembly 140 is in this final resting position (shown in FIG. 1), front stopper 141 and rear stopper 142 have displaced the entire contents of therapeutic agent chamber 160 and flush agent chamber 150, respectively, causing all of therapeutic agent 162 and flush agent 152 to be forced through outlet 124 and, for example, into a fluid flow line or other target connected thereto.

Figure 4:
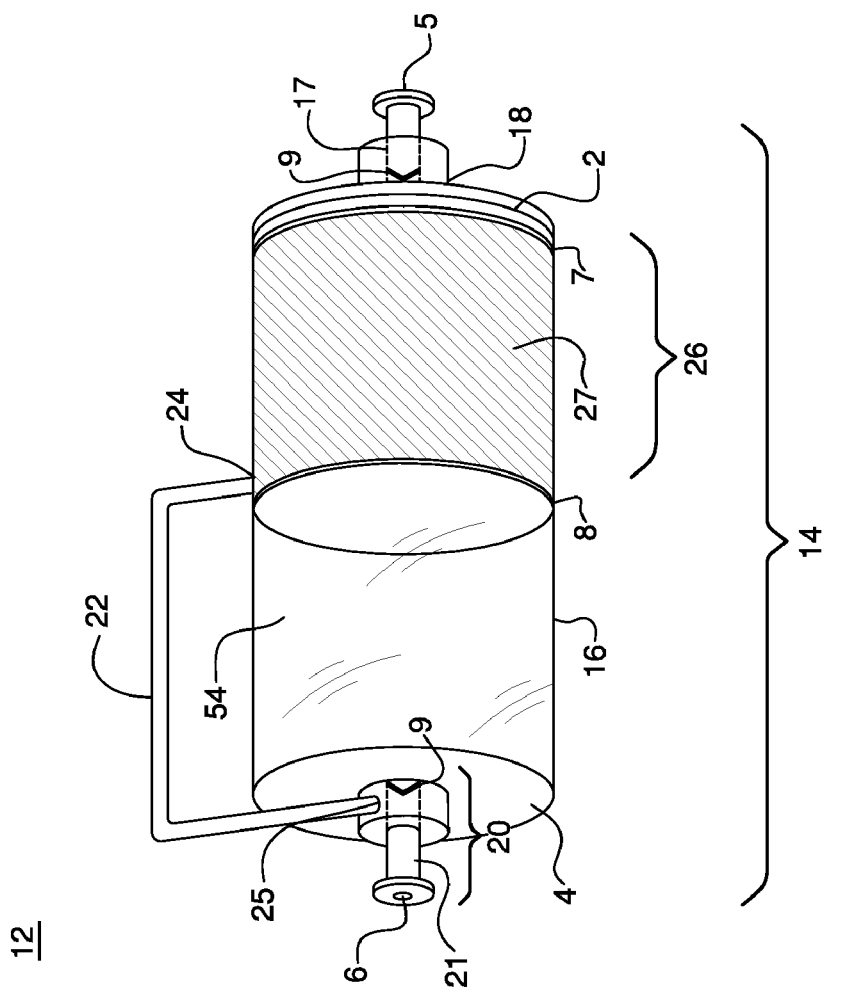
FIG. 4 is a perspective view of a first embodiment of a fluid delivery cartridge, with the stopper in the "ready" position within the chamber body.
Figure 5:
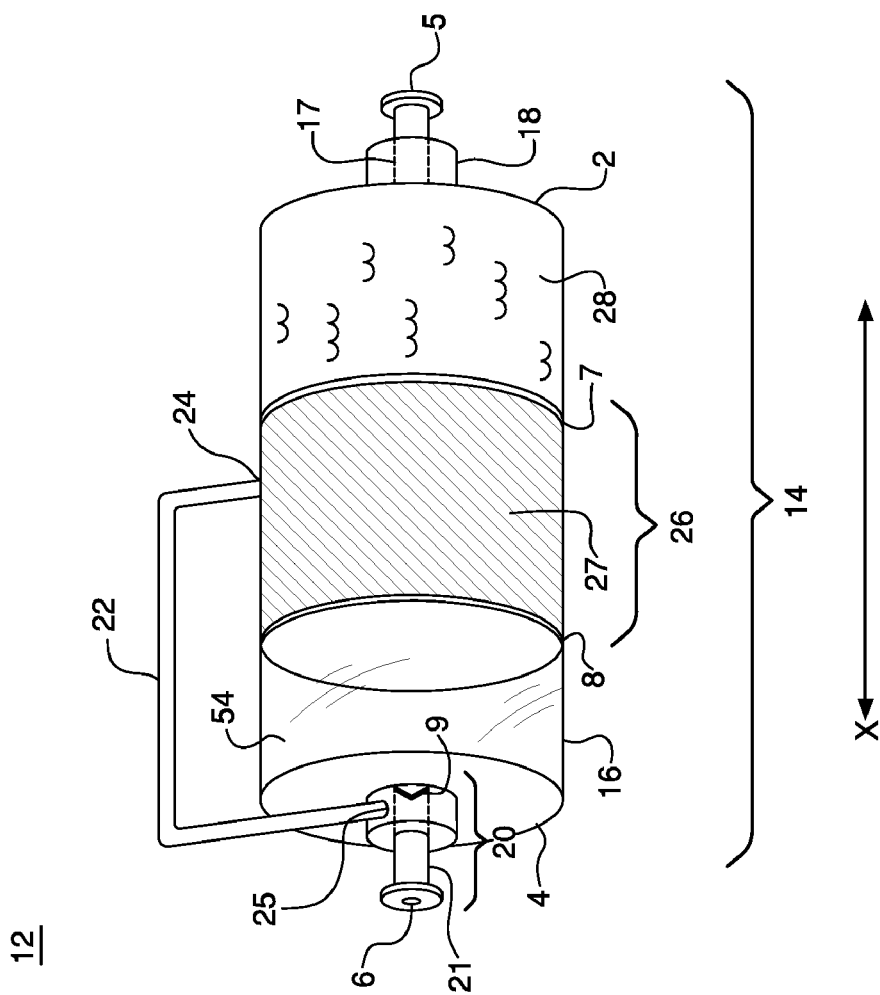
FIG. 5 is a perspective view of the fluid delivery cartridge depicted in FIG. 4, with the stopper in an intermediate position.
Figure 6:
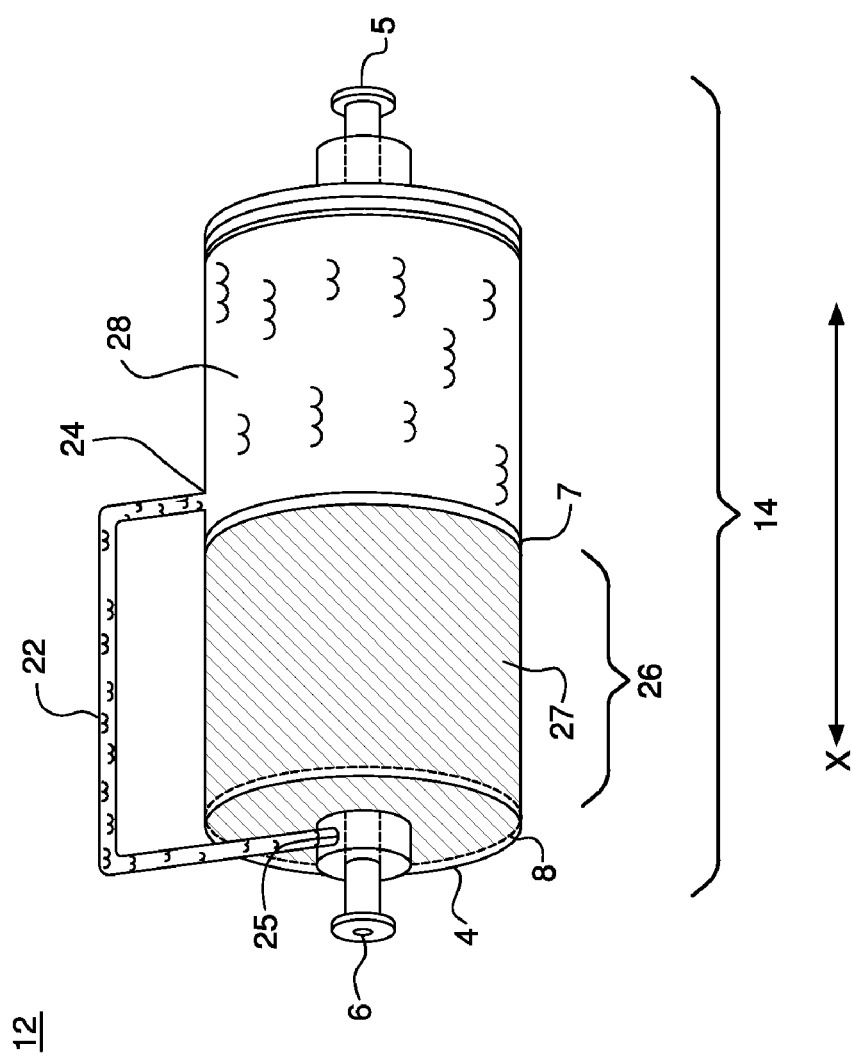
FIG. 6 is a perspective view of the fluid delivery cartridge depicted in FIG. 4, with the stopper in the "actuated" position.

As pictured in FIGS. 4-6, a fluid delivery device 10 may alternatively comprise a fluid administration cartridge 12 having an internal space defining a chamber 14. Cartridge 12 preferably is cylindrical having a fore and aft ends and a central portion disposed therebetween. For purposes of FIG. 4 and subsequent figures, the "aft" end is disposed at the right-hand portion of cartridge 12, and the "fore" end is at the left side of cartridge 12 through which fluid is discharged from chamber 14. Although the outer cross-sectional profile of cartridge 12 is preferably roughly circular, other cross-sectional profiles are also contemplated, including, for example, oval, octagonal, or square.

Chamber 14 includes a body 16, an inlet portion 18, and an outlet portion 20. Chamber body 16 is preferably cylindrical and includes aft 2 and fore 4 ends with circular cross-sections. However, the chamber body is not limited to the shape of chamber body 16 shown in FIG. 4. Other chamber body configurations are possible. For example, the chamber body may consist of a central chamber portion that is circular in cross section, tapered, and the like. The internal walls of chamber body 16 preferably are smooth.

Inlet portion 18 is located at the aft end of chamber 14 and forms a channel 17 that is in fluid communication with chamber body 16. Inlet portion 18 has a smaller cross-sectional area than chamber body 16. The inlet channel 17 formed by inlet portion 18 terminates in an opening 5 located that the far aft end of inlet portion 18. Both the internal bore and the external surface profile of the aft end of the inlet portion can be smooth and capable of engaging a syringe or fluid flow line in a "luer slip" configuration; alternatively, the external surface of the aft end of the inlet portion can feature threading in order to accommodate a syringe in a "luer lock" arrangement or any other structure for attaching a syringe, tubing, or other device, as will be understood by persons familiar with conventional fluid administration devices.

The internal channel 17 of inlet portion 18 can include a check valve 9 (FIGS. 4-6) that permits the flow of fluid in the direction of the chamber body 16, but not in the opposite direction. Thus, fluid that has been injected through the opening 5 of the inlet portion 18 and past the one-way valve 9 disposed in the internal channel 17 will not be able to flow in the opposite direction and back through the valve 9 towards the opening 5. Other means of preventing such "backflow" can also be used, various types of which will be readily recognized by persons familiar with conventional fluid administration devices Outlet portion 20 is located at the fore end 4 of chamber 14 and forms a channel 21 that is in fluid communication with chamber body 16. The internal cross-sectional profile of the channel 21 of outlet portion 20 will be typically smaller than that of chamber body 16. The internal channel 21 formed by outlet portion 20 terminates in an opening 6 located at the far fore end of outlet portion 20. The external profile of the fore end of the outlet portion is preferably smooth and capable of sealably engaging a fluid flow line such that fluid flowing through the opening of outlet portion will enter the fluid flow line, and no leakage will occur at the junction between outlet portion and the fluid flow line.

In a preferred embodiment, the inlet portion comprises a female luer connector, and the outlet portion comprises a male luer connector. Having an inlet portion that comprises a female component and an outlet portion that comprises a male component provides a safeguard against a user's confusion of the inlet portion with the outlet portion, especially in instances where the device is constructed from opaque materials and the fore end of the device is not readily visually distinguishable from the aft end. The preceding embodiment is preferred only, and the present devices are not limited to any particular combination of configurations for the inlet and outlet portions.

A bypass conduit 22 is a channel through which fluid can flow, and includes an inlet 24 and a terminus 25. Fluid enters bypass 22 through inlet 24, travels through the conduit, and exits the bypass through the terminus 25. A bypass can be formed from a bore through a solid substance, e.g., through drilling, can be constructed from hollow tubular material, or can be formed in accordance with other methods, a number of which are readily appreciated by those familiar with conventional fluid administration device fabrication. Bypass 22 preferably provides a fluid flow channel between chamber body 16 and outlet portion 20. Fluid can enter bypass 22 from chamber body 16 through bypass inlet 24 travel through the conduit portion of bypass 22, and exit the bypass and flow into outlet portion 20 through bypass terminus 25.

Stopper 26 comprises a movable barrier that may be solid or hollow and is constructed from at least one fluid-impermeable material. Exemplary fluid-impermeable materials include rubber, plastic, and combinations thereof. Stopper 26 is preferably cylindrical in shape, having leading 8 and trailing 7 ends each with substantially circular cross-sectional profiles, although the stopper may alternatively adopt other three-dimensional configurations, such as that of a polyhedron, e.g., a rectangular polyhedron having square or rectangular leading and trailing ends, to match corresponding shapes of the chamber 24.

A central portion 27 of stopper 26 is disposed between the leading 8 and trailing 7 ends, such central portion 27 preferably having a uniformly smooth surface profile to maximize slidable contact with mating surfaces and to prevent the flow of fluid therebetween. The surface of the central portion may comprise one or more annular ribs (not shown) disposed perpendicularly with respect to the longitudinal axis X of stopper 26. The ribs can circumscribe the central portion of the stopper at various locations along the length thereof such that only the ribs are in slidable contact with the inner surface of a rounded channel within which the stopper is emplaced. For example, the stopper may include one or more spaces or recesses that circumscribe the outer surface of stopper, with a rubber o-ring or gasket disposed within each space or recess, such that the outer edge of each o-ring or gasket contacts the interior surface of chamber body and thereby forms a seal about the entire circumference of the interior surface of chamber body.

Another possible configuration for the stopper comprises two or more discs each disposed perpendicularly to the longitudinal axis X of the cartridge, and joined by one or more support members that preserve the orientation of the discs and that cause the discs to move synchronously (i.e., prevent the discs from moving relative to one another). This stopper configuration can therefore resemble a barbell, with the "weights" being represented by the discs, and a support member fulfilling the role of the "bar" (although more than one support member may be employed in the current embodiment), the "weights" being fixably attached to the "bar". The outer edges of the discs preferably comprise material that creates a slidable seal between the outer edges and an external smooth surface; for example, the outer edges may comprise rubber. When the stopper of this configuration is deployed within a hollow channel, the space(s) between the discs are not exposed to the channel space(s) on the other side of the discs, and fluid cannot flow therebetween. Other surface profiles and configurations for the central portion may be used, with the proviso that the stopper 26 must be able to move relative to a surface with which it has contact, and that it should be able to prevent the flow of fluid from its trailing end to its leading end and vice versa.

Stopper 26 is disposed within chamber body 16 and is movable among different positions within chamber body 16. Stopper 26 prevents fluid communication between the portion of the chamber body that is located forward the leading edge 8 of stopper 26 and the portion of the chamber 14 (whether the chamber body 16 or the inlet portion 18) that is located behind the trailing edge 7 of stopper 26. Accordingly, stopper 26 can prevent fluid that flows into chamber body 16 via inlet portion 18 from reaching outlet portion 20. Stopper 26 preferably has a length in the longitudinal direction of cartridge 12 that is sufficient to block an inlet 24 of bypass channel 22, as described below.

FIG. 4 depicts stopper 26 in the "ready" position. In this position, the space within chamber body 16 forward the leading edge 8 of stopper 26 forms a drug compartment 54. Bypass conduit inlet 24 is blocked by stopper 26 such that drug compartment 54 is inaccessible by the portion of chamber 14 that is located behind the trailing edge of stopper 26. Bypass inlet 24 is located rearwards the drug compartment 54, and so material does not enter the bypass conduit 22 via the inlet 24.

Cartridge 12 can come preloaded with a desired quantity of drug substance disposed within drug compartment 54, or device 10 may be loaded with an agent by the administering personnel. A seal is created between stopper 26 and the interior wall of chamber body 16 such that material within drug compartment 54 cannot flow to portions of the chamber body 16 that are rearwards the drug compartment 54.

Figure 9:
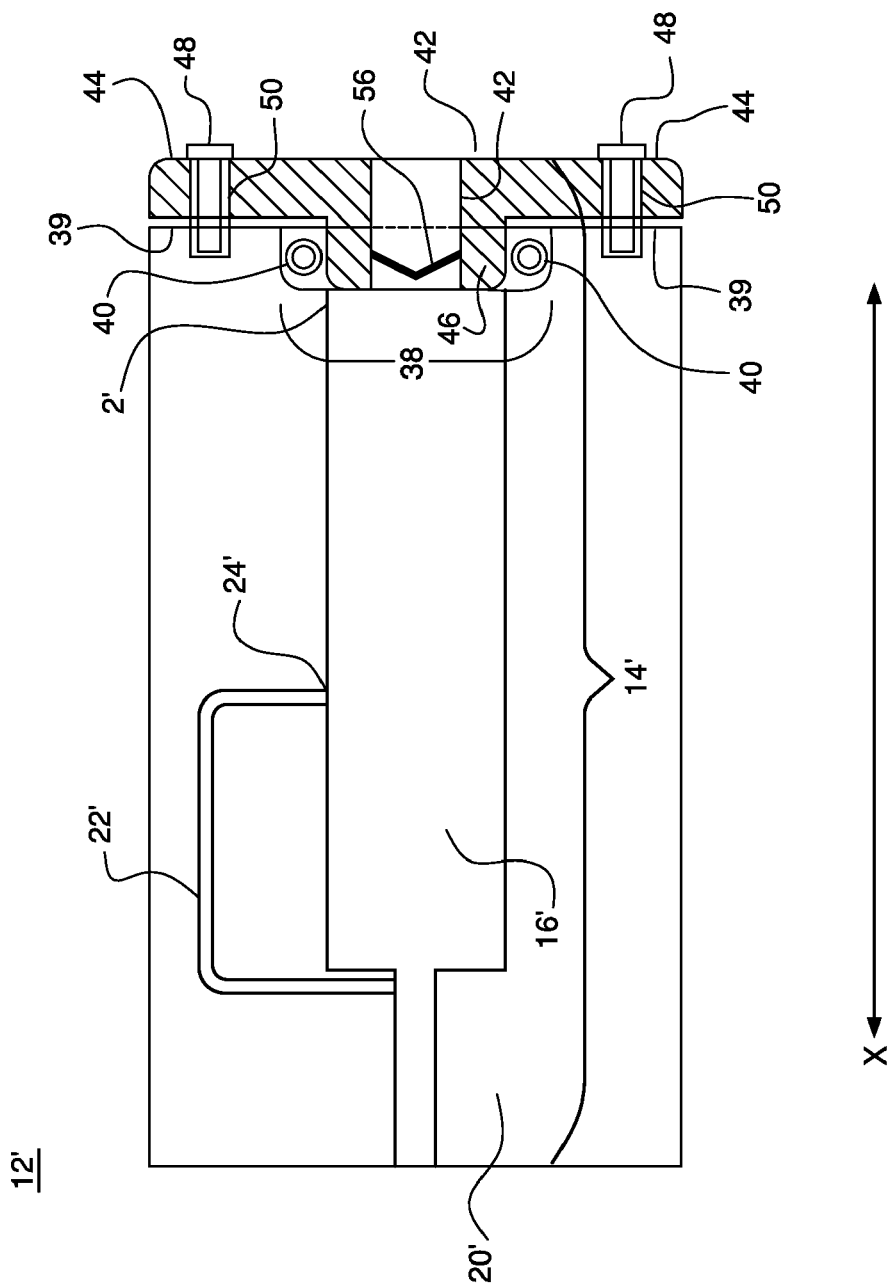
FIG. 9 is a longitudinal cross-sectional view of a fluid delivery cartridge constructed in accordance with a second embodiment.
Figure 10:
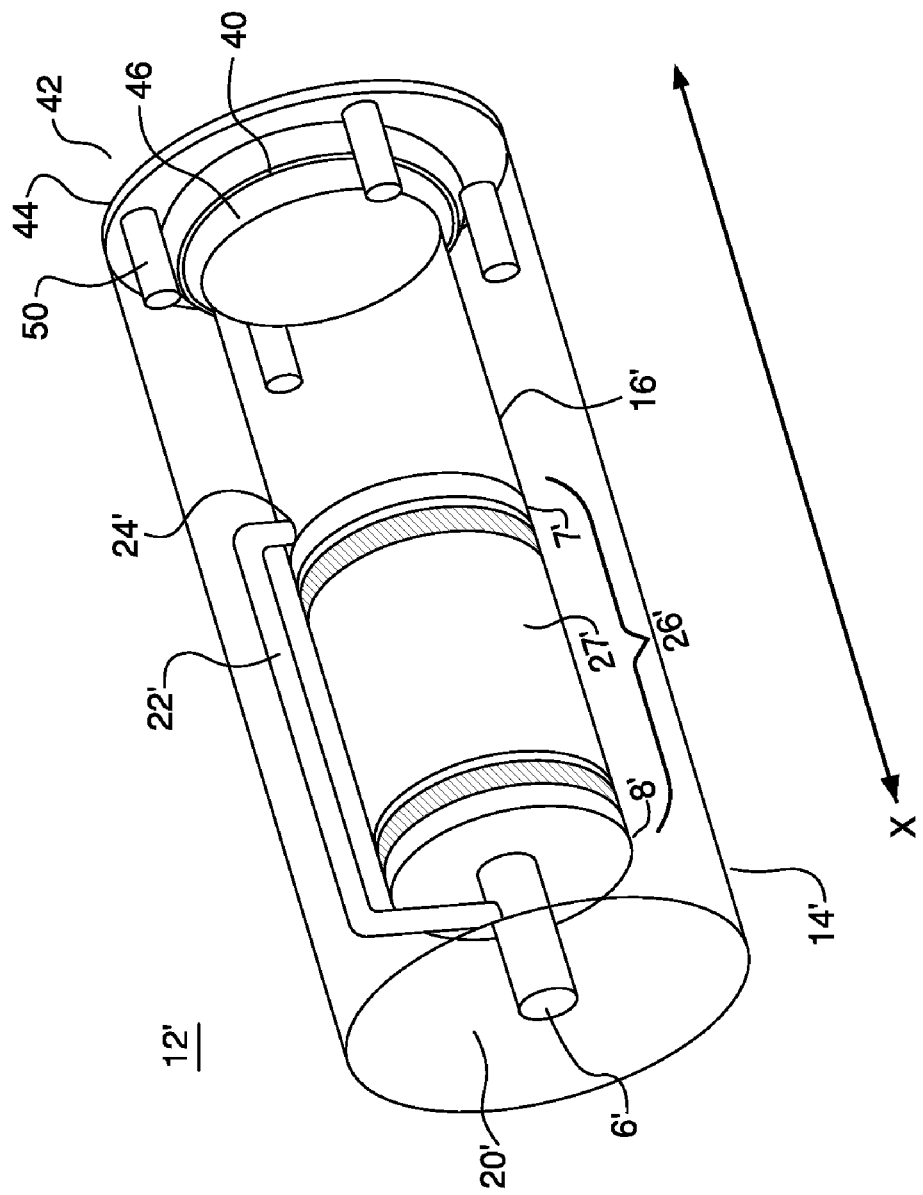
FIG. 10 is a transparent, perspective view of the fluid delivery cartridge depicted in FIG. 9.

Referring to FIGS. 9 and 10, a fluid delivery device is illustrated in accordance with another alternative embodiment. For instance, an inlet portion 18' comprises an opening at the aft end 2' of chamber body 16'. In this embodiment, the aft end of cartridge 12' includes a recess 38 for accommodating an o-ring 40 and a cap 42 that can be removably affixed to the aft end of cartridge 12' using one or more fasteners 48. Cap 42 preferably comprises a lip portion 44 and a plug portion 46. When installed at the aft end of cartridge 12', cap 42 is accommodated such that plug portion 46 is nested within recess 38 and lip 44 extends beyond recess 38 to at least partially cover the shelf 39 at the aft end of cartridge 12'. O-ring 40 can be disposed between the inner surface of recess 38 and the outer surface of plug portion 46 to seal the space between recess 38 and plug portion 46 and prevent the leakage of fluid between the components. In some embodiments, one or more fasteners 48 may extend through a corresponding fastener bore 50 that extends through lip portion 44 and into the aft end of cartridge 12'. Fastener bore 50 may be internally threaded to accommodate screw-like fasteners that may be reusably installed and removed as desired. In other embodiments, the inner surface of the recess is threaded and may be mated with a complementary threaded outer surface of plug portion. In such embodiments, the space between the lip and the shelf may be sealed using a gasket to prevent the leakage of fluid through such space.

A cap channel 52 completely extends through plug portion 46 of cap 42 to permit fluid communication between chamber 14' and an outside source of fluid. An inner end of cap channel 52 terminates at chamber inlet 18', and an outer end of cap channel 42 terminates at the outside surface of cap 32. Outer end of cap channel 42 can be configured to accommodate a syringe, fluid flow line, or other source of fluid, and to this end may include a luer connection (not shown). A check valve 56 (FIG. 9) is preferably disposed between chamber body 16' and outer end of cap channel 42 to prevent the flow of fluid from the chamber body 16' in the direction of the outer end of cap channel 42. Other means of preventing such "backflow" can also be used, various types of which are readily recognized by those skilled in the art.

Figure 7:
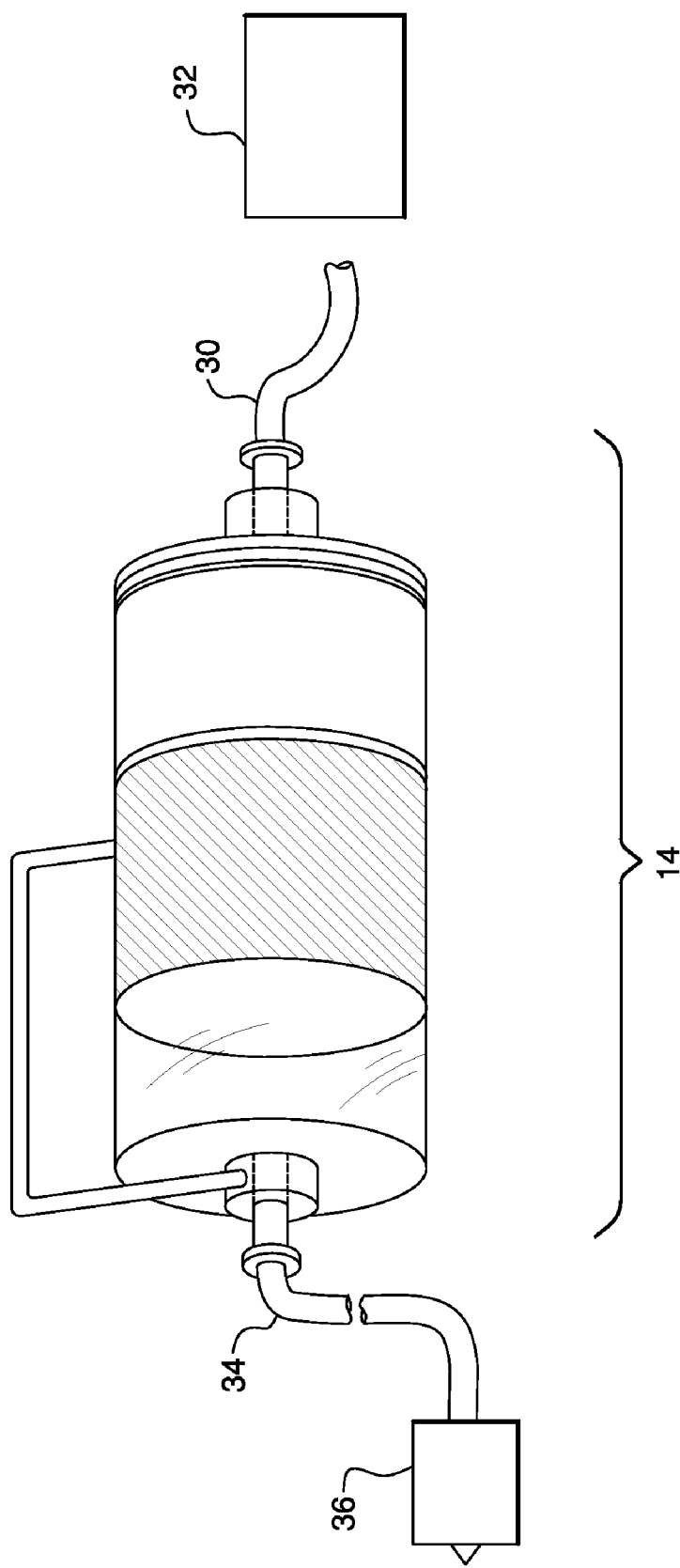
FIG. 7 illustrates the fluid delivery cartridge depicted in FIG. 4 associated with a fluid drive unit and inlet line at the inlet portion or "aft" end, and with an outlet fluid flow line and fluid delivery unit at the outlet portion or "fore" end.
Figure 8:
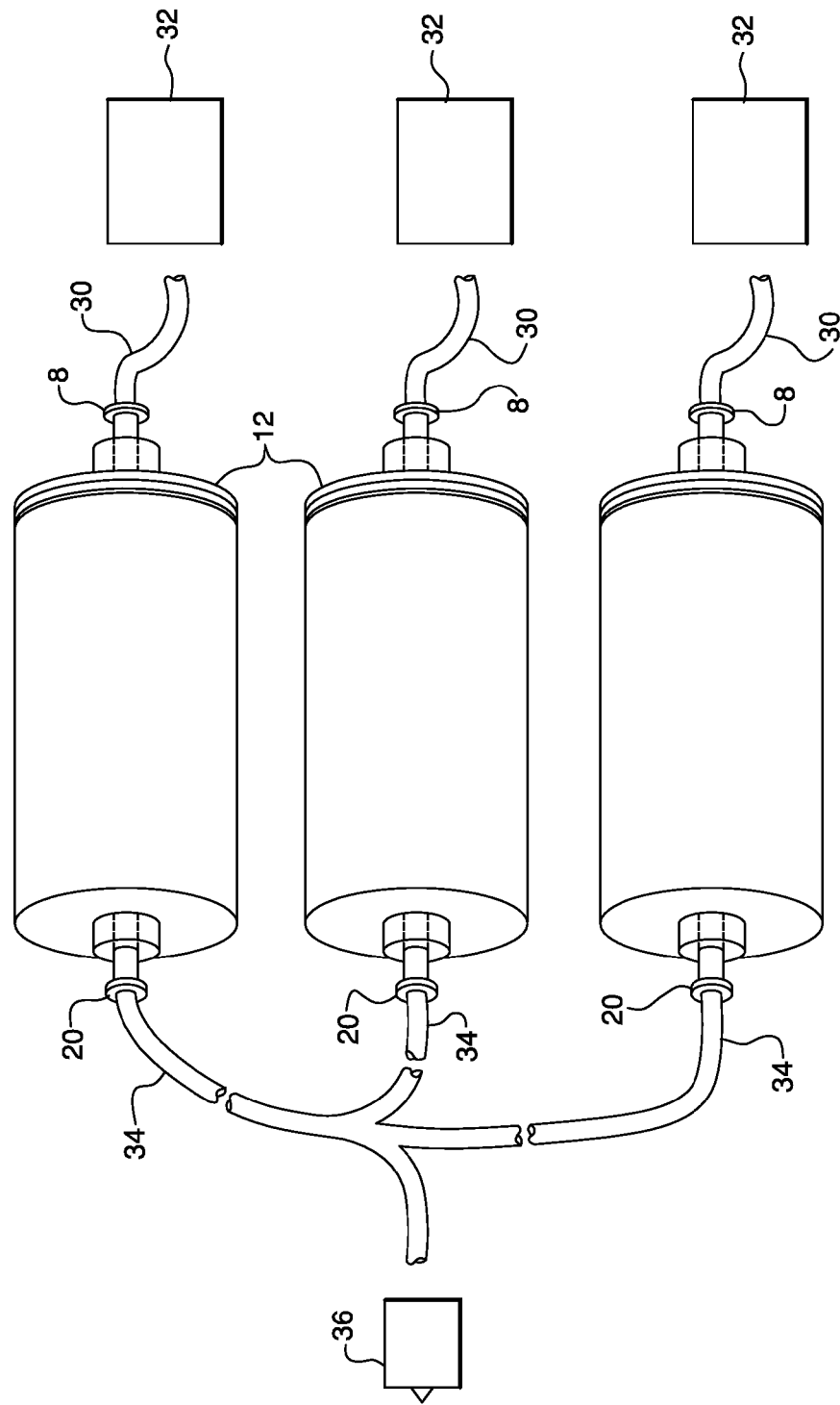
FIG. 8 is a set of three fluid delivery cartridges arranged in series, each associated with a fluid drive unit, inlet line, outlet lines, and a single fluid delivery unit.

Fluid, such as saline, can be forced through inlet portion 18, for example, by use of a syringe or fluid pump, or other fluid drive unit 32 (FIGS. 7 and 8). Where a syringe is used, fluid pressure is generated by the action of the syringe plunger, and fluid is forced through inlet portion 18 and into chamber body 16, thereby forming a fluid chamber 28 behind stopper 26 (FIG. 5). Stopper 26 is pushed towards the leading edge of cartridge 12 by the pressure generated by the introduction of pressurized fluid into chamber body 16, and in response thereto, the drug substance is forced from drug compartment 54 through outlet portion 20, which can be coupled to a fluid flow line such as an intravenous (IV) line 34 (shown in FIGS. 7 and 8). Although stopper 26 has moved to an intermediate position (shown in FIG. 5), bypass inlet 24 is still located rearwards the drug compartment 54, and because the trailing edge 7 of stopper 26 has not moved to a position that is forward the bypass inlet 24 and stopper 26 blocks bypass inlet 24, fluid cannot flow from fluid chamber 28 into bypass 22 (FIG. 5).

However, if a sufficient volume of fluid is forced through inlet 18 into fluid chamber 28, the resulting fluid pressure will cause stopper 26 to be moved to a position whereby the trailing edge 7 of stopper 26 is located forwards the bypass inlet 24, thereby no longer blocking inlet 24. Preferably, in the final phase of this "actuated" position (shown in FIG. 6), the stopper 26 has displaced the entire contents of drug compartment 54, causing all of the drug material to be forced through the outlet 20 and, for example, into a fluid flow line 34 (FIG. 7) connected thereto. Once the actuated stopper position has been reached, fluid communication between the fluid compartment 28 and bypass 22 will be enabled, and fluid can flow from the fluid compartment 28 into bypass 22 via inlet 24, and from the bypass 22 through terminus 25 and into outlet 20. Terminus 25 is located forward the one-way valve 9 disposed within outlet 20, and so fluid that enters outlet 20 from bypass 22 cannot flow back into chamber body 16 via the portion of outlet 20 located rearwards the one-way valve 9, and fluid pressure is maintained within fluid chamber 28 and bypass 22.

As stated previously, fluid can be forced through inlet 18 via syringe (not shown in the figures), a syringe or pump 32 coupled with a fluid flow line 30 (FIGS. 7 and 8), or by other means, numerous examples of which are readily ascertained by those skilled in the art.

When the stopper 26 is in the "actuated" position (FIG. 6), fluid can be continually perfused through inlet portion 18, into fluid chamber 28, through bypass 22 via bypass inlet 24, and through outlet 20. The total volume of fluid that may be perfused through the instant device is not limited to the capacity of a single fluid chamber, as the final position of the stopper 26 in the instant device does not block all fluid flow through the outlet 30. For example, a continual fluid source 32 can be placed in fluid communication with inlet 18 via a fluid flow line 30, and the amount of fluid that is perfused through chamber 14, through bypass 22, and through outlet 20 can therefore be effectively limitless.

For delivery of multiple doses of drug or multiple different drug substances, a plurality of cartridges may be arranged in series, each in fluid communication with an inlet line 30 and fluid drive unit 32 through their respective inlets 18, and an outlet line 34 and fluid delivery unit 36 via their respective outlets 20 (FIG. 8). Each cartridge 12 can be associated with an inlet line 30 and a fluid drive unit 32 (FIG. 8), or alternatively, a single fluid drive unit can be used to deliver fluid to each of the cartridges 12 in the series arrangement (not shown). For example, if a series of three cartridges are used, a first drug substance, a second drug substance, and a third drug substance, respectively, may be preloaded into the drug compartments 54 of the cartridges, and this arrangement can be used to deliver the drug contents of the respective cartridges simultaneously, two at a time, or in fully staggered fashion. The inventive devices impose no limitations on the potential choices for such arrangements.

An inventive cartridge can be used in conjunction with any dedicated line, including but not limited to an IV line, a catheter, or a central line. As used herein, the phrase "dedicated line" generally refers to any line for the delivery of fluid. Therefore, in preferred embodiments, the inventive devices can be used as a component in any fluid delivery system that includes a dedicated line. In preferred embodiments, the inlet, outlet, or both are adapted for connection to a dedicated line.

The delivery of fluid to the disclosed cartridges may be accomplished through the use of any "fluid drive unit" which, as used herein, refers to any mechanism that is capable of transferring a fluid from a source that is external to the disclosed cartridges to the inlet 18 of the disclosed device. A syringe is but one form of fluid drive unit; another is a pump. Injection of fluids is well known among both medical and manufacturing practitioners, and the fluid drive unit may be chosen according to the particular needs of the relevant process. A fluid drive unit may be operated manually, but in some instances the appliance will be part of an automated procedure and will be preset and pre-timed to transfer fluid(s) into the cartridge or series of cartridges in a desired sequence, repeated as many times as required. Injection from a syringe is a preferred means for introducing a fluid to the inventive device. A "syringe" may comprise the familiar tubular medical instrument, or may comprise a gun-like apparatus with one or more chambers, each chamber capable of accommodating one or more fluids. Gun-like syringe devices are known in the art, and are typically operated by the manual depression of a trigger or through preset commands that result in the automatic discharge of the contents of the chambers, either one by one (sequentially—appropriately timed and in an order that is predetermined by the device operator), or simultaneously (again, at a predetermined time). The provided delivery devices and methods are therefore intended for use with fluid drive units as described herein.

The construction of the instant cartridges can be accomplished in accordance with techniques that are widely understood among those skilled in the art. The cartridge and its various components as described herein may be molded from suitable materials, such as various plastic materials, using such molding techniques as thermoplastic and thermoset injection molding, blow molding, rotational molding, thermoforming, structural foam molding, compression molding, resin transfer molding (RTM), or others. Alternatively, the cartridge and components may be machined, for example, by drilling passages for such features as bypass 22', chamber 14', fastener bore 50, etc (FIG. 10). A combination of molding and machining techniques can also be used. The chamber and bypass line may be formed from a continuous block. For example, the manufacturer may form the chamber and bypass line by hollowing out portions of a single block of material, or the manufacturer may form the chamber and bypass line by hollowing out half of these structures from a first block, the other half of these structures from a second block, and then joining the first and second blocks to form complete chamber and bypass structures. All methods of constructing the chamber and bypass structures (and the other structures of the instant devices) are contemplated as being within the scope of the present invention.

One advantage of the instant device is that despite the novel concepts employed and advantageous characteristics possessed thereby, the mechanical design is straightforward, and those skilled in the art can readily apprehend how the cartridge and its components as described herein may be prepared from suitable materials. Preferable materials include those that are compatible with medical treatment of human subjects, and to this end, polypropylene is a preferred material for many of the components of the present device. With regard to the stopper 26, 26', that component preferably includes one or more sections, such as ribs or discs, that provide a slidable seal with the interior wall of chamber body 16, 16'; these sections can comprise any suitable material or combination of materials, including natural or synthetic "rubber", such as, for example, Kalrez®, Simriz®, Viton®, Chemraz®, silicone, neoprene, and/or nitrile. The materials used for the construction of valves, fasteners, and connectors/luers, as well as the methods for the construction thereof, are readily appreciated by those skilled in the art, and all appropriate materials and means of construction are contemplated herein.

Also provided are methods for delivering a therapeutic agent comprising the steps of pressurizing the therapeutic agent within a drug chamber by introducing a working fluid into a working chamber that is separated from the drug chamber by a movable stopper, the stopper responding to the introducing of the working fluid into the working chamber by pressurizing the therapeutic agent; wherein said pressurizing forces the therapeutic agent into a delivery channel via an outlet port that is in fluid communication with the drug chamber; and, wherein the introducing of the working fluid into the working chamber moves the stopper to a position whereby the working fluid can flow between the working chamber and the delivery channel via a bypass conduit. The working fluid can comprise, for example, a diluent or carrier (such as saline), or can comprise a beneficial agent, such that the administration of the therapeutic agent as delivered from the drug chamber can be followed by the administration of a second therapeutic agent as delivered from the working chamber.

Also disclosed are methods of delivering a fluid agent comprising the steps of providing a cartridge including a working fluid chamber proximate a cartridge inlet, a fluid agent chamber proximate a cartridge outlet, a moveable stopper therebetween, and a bypass conduit; introducing a working fluid into the working chamber such that the stopper moves from a ready position, in which the stopper blocks flow from entering the bypass conduit, in the direction of the cartridge outlet to an actuated position, whereby the stopper movement (i) pushes at least a portion of the fluid agent from the cartridge and (ii) unblocks the bypass conduit to enable working fluid flow from the working fluid chamber. The working fluid can comprise, for example, a diluent or carrier (such as saline), or can comprise a beneficial agent, such that the administration of the fluid agent as delivered from the fluid agent chamber can be followed by the administration of a therapeutic agent as delivered from the working fluid chamber.

The disclosures of each patent, patent application and publication cited or described in this document are hereby incorporated herein by reference, in their entirety.

The foregoing description is provided for the purpose of explanation and is not to be construed as limiting the invention. While the invention has been described with reference to preferred embodiments or preferred methods, it is understood that the words which have been used herein are words of description and illustration, rather than words of limitation. Furthermore, although the invention has been described herein with reference to particular structure, methods, and embodiments, the invention is not intended to be limited to the particulars disclosed herein, as the invention extends to all structures, methods and uses that are within the scope of the appended claims. Those skilled in the relevant art, having the benefit of the teachings of this specification, may effect numerous modifications to the invention as described herein, and changes may be made without departing from the scope and spirit of the invention as defined by the appended claims.

What is claimed:

1. A dual-stopper syringe, comprising:
a chamber, including an outlet and a bypass channel having a front end and a rear end;
a front stopper and a rear stopper, wherein the chamber, the front stopper, and the rear stopper define a flush agent chamber and a therapeutic agent chamber;
a piston attached to the rear stopper; and
a rod including a backstop and attached to the front stopper, wherein the rod penetrates through the rear stopper such that the rear stopper is adapted to slide along the rod between the front stopper and the backstop;
wherein the flush agent chamber is adapted to draw a flush agent into the flush agent chamber while the piston is being pulled away from the outlet; and
wherein the therapeutic agent chamber is adapted to draw a therapeutic agent into the therapeutic agent chamber, after the flush agent chamber is fully filled with a flush agent, while the piston is pulled away from the outlet.

2. The dual-stopper syringe of claim 1 wherein the outlet includes an outlet channel extending from the syringe body, and the front end of the bypass channel is connected to the outlet channel.

3. The dual-stopper syringe of claim 1 wherein the therapeutic agent is adenosine.

4. The dual-stopper syringe of claim 1 wherein the flush agent is saline.

5. The dual-stopper syringe of claim 1 wherein the flush agent comprises a useful agent.

6. The dual-stopper syringe of claim 1 wherein the chamber is defined by the inside of a cylindrical barrel and the bypass channel extends outwardly from an exterior surface of the cylindrical barrel.

7. The dual-stopper syringe of claim 1 wherein the outlet channel comprises a male luer fitting.

8. The dual-stopper syringe of claim 1 wherein the outlet channel is adapted for connection to a dedicated line.

9. A dual-stopper syringe, comprising:
a chamber including an outlet;
a bypass channel having a front end and rear end; and
a stopper assembly, including:
a front stopper,
a rear stopper,
a piston attached to the rear stopper and adapted to receive a pushing or pulling action from a user to actuate the syringe, and
a rod including a backstop, the rod being affixed to the front stopper and slidably connected to the rear stopper, the rod slidably penetrating through the rear stopper such that the rear stopper is adapted to slide along the rod between the front stopper and the backstop, the backstop limiting the rearward movement of the rear stopper relative to the front stopper;
the syringe capable of having an unloaded position, a flush agent loading position, and a therapeutic agent loading position, such that
in the unloaded position, the front stopper and the rear stopper are located proximate the chamber outlet,
in the flush agent loading position, the front stopper is located proximate the chamber outlet, the rear stopper is spaced apart from the front stopper to define a flush chamber, and the rear end of the bypass channel is open to the flush chamber,
in the therapeutic agent loading position, the front stopper is spaced apart from the outlet to define a therapeutic agent chamber, the rear stopper is spaced apart from the front stopper and located proximate the backstop, and the rear end of the bypass channel is either blocked by the front stopper or open to the therapeutic agent chamber;
whereby in the unloaded position and the flush agent loading position, the piston moves the rear stopper away from the outlet and away from the front stopper when pulled, and
whereby in the therapeutic agent loading position, the piston moves the front stopper and rear stopper away from the outlet when pulled.

10. A method comprising the steps of:
providing a chamber, including an outlet and a bypass channel having a front end and a rear end;
providing a front stopper, a rear stopper, and a piston attached to the rear stopper, wherein the chamber, the front stopper, and the rear stopper define a therapeutic agent chamber and a flush agent chamber;
providing a rod including a backstop, the rod being attached to the front stopper and penetrating through the rear stopper, such that the rear stopper is adapted to slide along the rod between the front stopper and the backstop;
wherein the front stopper is adapted to slide away from the outlet and block the rear end of the bypass channel when the piston is pulled away from the outlet such that the rear stopper pulls the rod away form the outlet.

11. A method of loading a syringe, comprising the steps of:
(a) providing a chamber, including an outlet and a bypass channel having a front end and a rear end;
(b) providing a front stopper, a rear stopper, and a piston attached to the rear stopper, wherein the chamber, the front stopper, and the rear stopper define a therapeutic agent chamber and a flush agent chamber;
(c) providing a rod including a backstop, the rod being attached to the front stopper and penetrating through the rear stopper, such that the rear stopper is adapted to slide along the rod between the front stopper and the backstop;
(d) positioning the front stopper and rear stopper in a fully-actuated position;
(e) loading a flush agent into the flush agent chamber by pulling the piston away from the outlet until the front stopper blocks the rear end of the bypass channel; and
(f) loading a therapeutic agent into the therapeutic agent chamber by pulling the piston away from the outlet.

12. A plunger-less fluid administration cartridge comprising:
a chamber having a body, an inlet port, and an outlet port at opposing ends;
a bypass line connecting the chamber body to the outlet port and enabling flow therebetween;
a barrier stopper located in the chamber body and movable between a ready position and an actuated position;
the stopper, in the ready position, (i) is spaced apart from the outlet port to form a drug compartment of the chamber and (ii) blocks flow of a working fluid into the bypass line;

the stopper, in the actuated position, is located proximate the outlet port and enables flow of the working fluid through the bypass line from the inlet port to the outlet port; and, whereby moving the stopper from the ready position to the actuated position ejects fluid from the drug compartment through the outlet port.

13. The cartridge of claim 12 wherein the stopper is actuated from its ready position to its actuated position by flow of the working fluid through the inlet port.

14. The cartridge of claim 12 wherein the actuated position constitutes the final resting position of the stopper.

15. The cartridge of claim 12 wherein the outlet port includes an outlet channel extending from the cartridge body, and the bypass line is connected to the outlet channel.

16. The cartridge of claim 12 wherein the cartridge, while the stopper is in its actuated position, enables continuous fluid flow from the inlet port, through the bypass line around the stopper, and out the outlet port.

17. The cartridge of claim 12 wherein the working fluid is saline.

18. The cartridge of claim 17 wherein the agent is adenosine.

19. The cartridge of claim 12 wherein the working fluid comprises a useful agent.

20. The cartridge of claim 12 wherein the cartridge includes a housing that defines the chamber, the bypass line includes an inlet connected to the housing, and the stopper blocks the bypass line inlet in its ready position and uncovers the bypass line inlet in its actuated position.

21. The cartridge of claim 12 wherein the chamber has a cylindrical housing and the bypass line extends outwardly from an exterior surface of the housing.

22. The cartridge of claim 12 wherein the chamber and bypass line are formed from a continuous block.

23. The cartridge of claim 12 wherein cartridge further comprises a cap at least partially covering an end of the cartridge body, and an opening in the cap forms at least a portion of the inlet port.

24. The cartridge of claim 12 wherein the inlet port and outlet port include luer fittings.

25. The cartridge of claim 24 wherein the inlet port comprises a female luer fitting and the outlet port comprises a male luer fitting.

26. The cartridge of claim 12 wherein the inlet port, outlet port, or both are adapted for connection to a dedicated line.

27. A fluid delivery device comprising:
a cartridge having a central chamber, the chamber having first and second opposing ends,
a fluid inlet disposed at the first end of said central chamber;
an outlet channel disposed at the second end of said central chamber, and a fluid outlet disposed between said central chamber and said outlet channel and permitting fluid flow between said central chamber and said fluid outlet;
a bypass conduit permitting fluid flow directly between said central chamber and said outlet channel and not via said fluid outlet;
a stopper disposed within said central chamber, said stopper being capable of moving through a first and second stage in response to fluid pressure that is caused by fluid traveling through said fluid inlet and into said central chamber,
wherein said first stage comprises moving within said central chamber in the direction away from said first end of said central chamber, and
wherein said second stage comprises moving within said central chamber whereby said stopper is positioned such that fluid can flow from said central chamber into said bypass conduit.

28. A method of delivering a therapeutic agent comprising the steps of:
pressurizing said therapeutic agent within a drug chamber by introducing a working fluid into a working chamber that is separated from said drug chamber by a movable stopper, said stopper responding to the introducing of said working fluid into said working chamber by pressurizing said therapeutic agent;
wherein said pressurizing forces said therapeutic agent into a delivery channel via an outlet port that is in fluid communication with said drug chamber;
and, wherein the introducing of the working fluid into the working chamber moves said stopper to a position whereby the working fluid can flow between said working chamber and said delivery channel via a bypass conduit.

29. A method of delivering a fluid agent comprising the steps of:
providing a cartridge including a working fluid chamber proximate a cartridge inlet, a fluid agent chamber proximate a cartridge outlet, a moveable stopper therebetween, and a bypass conduit; and,
introducing a working fluid into the working chamber such that the stopper moves from a ready position, in which the stopper blocks flow from entering the bypass conduit, in the direction of the cartridge outlet to an actuated position, whereby said stopper movement (i) pushes at least a portion of the fluid agent from the cartridge and (ii) unblocks the bypass conduit to enable working fluid flow from the working fluid chamber.

* * * * *